United States Patent [19]
Haapalinna et al.

[11] Patent Number: 5,902,807
[45] Date of Patent: May 11, 1999

[54] METHOD FOR THE TREATMENT OF MENTAL ILLNESS IN MAMMALS AND A COMPOSITION THEREFOR

[75] Inventors: Antti Haapalinna, Hellaksenkatu 4 D 5, Fin-23060 Turku; Timo Viitamaa, Turku; Jukka Sallinen, Turku; Mika Scheinin, Naantali; Juha-Matti Savola, Turku, all of Finland

[73] Assignee: Antti Haapalinna, Finland

[21] Appl. No.: 08/854,730

[22] Filed: May 12, 1997

[51] Int. Cl.$^6$ .......................... A61K 31/55; A61K 31/505
[52] U.S. Cl. ............................................. 514/220; 514/258
[58] Field of Search ...................................... 514/220, 258

[56] References Cited

FOREIGN PATENT DOCUMENTS 730865   9/1996   European Pat. Off. .

OTHER PUBLICATIONS

Angst, J. et al., "Double blind study with HF 1854 (8–chloro–11–(4–methyl–1–piperazinyl)–5H–dibenzo diazepine) in comparison with levomepromazine", Pharmakopsychiat./Neuro–Psychopharmakol. 4(4), 1971, pp. 192–200, an abstract from Caplus, An 1972:196.

Angst, J. et al., "Ergebnisse eines Doppelblindversuches von HF 1854* (8–Chlor–11–(4–methyl–1–piperazinyl)–5H–dibenzo (b, e) (1,4) diazepin) im Vergleich zu Levomepromazin", Pharmakopsychiat./Neuro–Psychopharmakol. vol. 4, 1971, pp. 192–200, Georg Thieme Verlag, Stuttgart.

Spivak, B. et al., "Reduction of Aggressiveness and Impulsiveness during Clozapine Treatment in Chronic Neuroleptic–Resistant Schizophrenic Patients", Clinical Neuropharmacology 20(5), 1997, pp. 442–446.

Sallinen, J. et al., "Adrenergic $\alpha_{2C}$–Receptors Modulate the Acoustic Startle Reflex, Prepulse Inhibition, and Aggression in Mice", Journal of Neuroscience 18(8), 1998, pp. 3035–3042.

Lott et al, Chemical Abstracts, vol. 126, abstract no. 84506, 1996.

Inoue et al, Chemical Abstracts, vol. 126, abstract No. 14642, 1996.

Blin et al, Chemical Abstracts, vol. 125, abstract No. 212567, 1996.

*Primary Examiner*—William R. A. Jarvis
*Attorney, Agent, or Firm*—Finnegan, Henderson, Farabow, Garrett & Dunner, L.L.P.

[57] ABSTRACT

The invention relates to a method for treating a mammal suffering from mental illness induced by propagation of stress, said method comprising the step of removing or diminishing the tone of the endogenous alpha-2C-adrenoceptors in the central nervous system of said mammal. The invention relates further to pharmaceutical compositions useful for said treatment.

12 Claims, 4 Drawing Sheets

METHOD FOR THE TREATMENT OF MENTAL ILLNESS IN MAMMALS AND A COMPOSITION THEREFOR

FIELD OF THE INVENTION

This invention relates to a method for the treatment of mental illness in mammals and compositions therefor. More specifically, the invention relates to methods and compositions useful to remove or diminish the tone of the endogenous alpha-2C-adrenoceptors in the central nervous system.

BACKGROUND OF THE INVENTION

The publications and other materials used herein to illuminate the background of the invention, and in particular, cases to provide additional details respecting the practice, are incorporated by reference.

Conventionally antagonists of alpha-2-adrenoceptors, such as yohimbine, have been found to be anxiogenic (1). Three subtypes, namely alpha-2A-, alpha-2B- and alpha-2C-adrenoceptors have been discovered in human. A fourth subtype, an alpha-2D-adrenoceptor, is known in rat and bovine. According to literature, most of the known alpha-2-adrenoceptor antagonists are not specific to any certain subtype (alpha-2A to alpha-2D). As examples of such non-specific alpha-2-adrenoceptor antagonists can be mentioned rauwolscine, yohimbine, idazoxan, atipamezole and RX821002 (reference 6, Marjamäki et al.).

However, because alpha-2-adrenoceptor subtypes have a discrete pattern of distribution in the brain (2) so that the alpha-2C-adrenoceptor appears to be distributed along the limbic system (a complex brain area related to affections and other mental functions), we made a hypothesis that a behavioural response of a subtype C selective alpha-2-adrenoceptor antagonist would be different from that of a non-subtype selective.

OBJECT AND SUMMARY OF THE INVENTION

The object of the present invention is to provide a method for treating a mammal suffering from mental illness induced by propagation of stress, particularly a mental illness which is clinically expressed as anxiety, stress, post-traumatic stress disorder, affective flattening, anhedonia, alogia, avolition, aggressivity, or impairment of cognitive function initiated by stress-induced neuronal degeneration.

The object is further to provide a method for treating a mammal suffering from mental illness induced by propagation of stress without substantially eliciting sedative or hypotensive effects or altering motor functions in said mammal.

The present invention thus concerns a method for treating a mammal suffering from mental illness induced by propagation of stress, said method comprising the step of removing or diminishing the tone of the endogenous alpha-2C-adrenoceptors in the central nervous system of said mammal.

Furthermore, this invention concerns a pharmaceutical composition, or a derivative thereof, useful for the treatment of mental illness induced by propagation of stress in a mammal, said composition comprising a therapeutically effective amount of an alpha-2-adrenoceptor antagonist which is selective to the alpha-2C-adrenoceptor, in combination with a pharmaceutically acceptable excipient.

BRIEF DESCRIPTION OF THE DRAWINGS

FIG. 4A and 4B show the effect of alteration of the alpha-2C-adrenoceptor function at the gene expression level in mice.

DETAILED DESCRIPTION OF THE INVENTION

The present invention relates to a novel therapeutic approach to treat disturbance of mental health in mammals. The results to be presented below show that stress-induced anxiety and subsequent mental disturbances can be prevented by means which remove or diminish the tone of the endogenous alpha-2C-adrenoceptors in the central nervous system of said mammal.

New therapeutic agents selectively blocking the alpha-2C-adrenoceptors in the limbic system and removing or diminishing propagation of mental stress reaction, provide a new approach to protective anxiolytic therapy and a novel method of treatment of patients suffering from mental disturbance clinically expressed as, for example, anxiety, stress, post-traumatic stress disorder, affective flattening, anhedonia, alogia, avolition, aggressivity, or impairment of cognitive function initiated by stress-induced neuronal degeneration.

Furthermore, the alpha-2C-adrenoceptor antagonist selective to the alpha-2C-adrenoceptor used in combination with an anxiolytic, antidepressive or antipsychotic compound (which compound does not need to be an antagonist selective to the alpha-2C-adrenoceptor) would be therapeutically beneficial by providing either an effective treatment to patient resistant to the said conventional therapeutic agents alone, or by providing a synergistic action with the said conventional therapeutic agents.

The alpha-2-adrenoceptor antagonist selective to the alpha-2C-adrenoceptor and the second compound should preferably be administered to the patient during the same period of treatment.

Most preferably, the alpha-2-adrenoceptor antagonist selective to the alpha-2C-adrenoceptor and the second compound should be administered simultaneously. According to a particularly preferable embodiment, these compounds are administered from the same dosage form.

Such a combination therapy will allow the use of smaller doses of the said compounds and thereby substantially reduce their sedative effects, their disturbance on motor functionality, and other adverse effects such as hypotensive effects.

Suitable alpha-2C-adrenoceptor antagonists selective to the 2C-adrenoceptor are known in literature. As examples can be mentioned MK-912 (5) and BAM-1303 (12). According to our own investigations, clozapine and risperidone have also been found to possess high selectivity to the alpha-2C-adrenoceptor. Preferably, the antagonist should have a selectivity to the alpha-2C-adrenoceptor of at least the same level as MK-912, i.e. a ten-fold preference to the alpha-2C subtype over the other alpha-2-subtypes.

For the purpose of the invention, the alpha-2-adrenoceptor antagonist selective to the alpha-2C-adrenoceptor or its pharmaceutically acceptable derivative (such as salt, ester, or the like) can be administered by various routes. The suitable administration forms include, for example, oral formulations; parenteral injections including intravenous, intramuscular, intradermal and subcutanous injections; transdermal or rectal administration forms.

The required dosage of the compounds of the alpha-2C subtype selective antagonist will vary with the particular condition being treated, the severity of the condition, the duration of the treatment, the administration route and the specific compound being employed. The therapeutically effective dose for a particular compound can, for example, be established according to the method described in Experiment 1 below.

Figure 1:
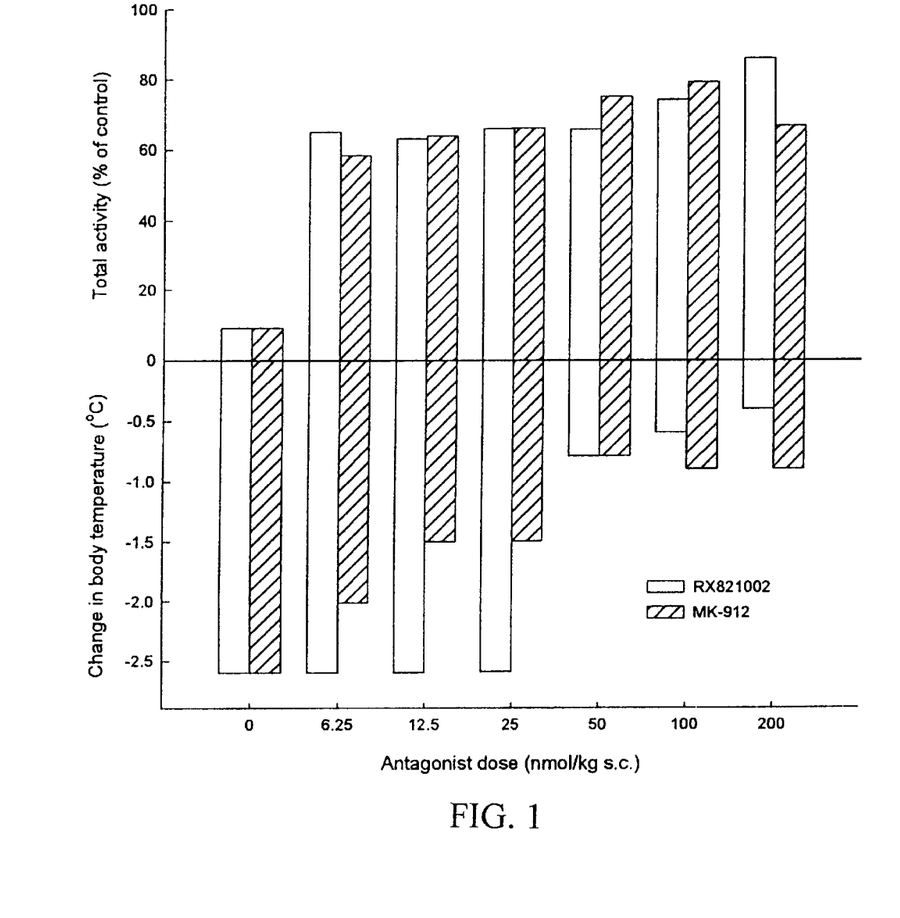
FIG. 1 shows the antagonism of dexmedetomidine-induced sedation (upper graph) and of hypothermia (lower graph) by previous administration of RX821002, an alpha-2-adrenoceptor antagonist not selective to the alpha-2C-adrenoceptor, (open bars) or MK-912, an alpha-2-adrenoceptor antagonist selective to the alpha-2C-adrenoceptor (hatched bars).

In order to elucidate the role of a certain alpha-2-adrenoceptor subtype, pharmacological profile at the other subtypes should be fixed to the same extent. We had established such an experimental bioequivalence method which allows to study profile differences of alpha-2-antagonists acting on alpha-2-adrenoceptors other than alpha-2A-adrenoceptors. Locus coeruleus is a brain nucleus which is almost exclusively occupied by the alpha-2A-adrenoceptor subtype and which mediates sedation induced by dexmedetomidine (an agonists of alpha-2-adrenoceptors) (3). Secondly, work with transgenic mice had indicated that the alpha-2C-adrenoceptor subtype is contributing to the hypothermia induced by non-selective agonists of alpha-2-adrenoceptors (4). We used this information to find a dose of a potential alpha-2C-adrenoceptor subtype selective antagonist which would equally antagonise the alpha-2A-adrenoceptor-mediated sedation in comparison to a nonsubtype selective alpha-2-adrenoceptor antagonist. Literature information has indicated that MK-912 (also known as L-657,743) shows approximately a ten-fold preference to the alpha-2C-subtype over the other alpha-2-adrenoceptors (5) and that the affinity to the alpha-2A and alpha-2B-adrenoceptor is equal. In comparison to a nonsubtype selective alpha-2-adrenoceptor antagonist RX821002 (with equally high affinity to all the alpha-2-adrenoceptor subtypes) (6) we found that there was a clear difference in the ability of the alpha-2C-adrenoceptor antagonist MK-912 to antagonise dexmedetomidine induced hypothermia compared to dexmedetomidine-induced sedation (see FIG. 1 of Experiment 1 presented below), fitting with the evidence obtained with the transgenic mice.

Based on the bioequivalence study of Experiment 1 below we could conclude that both MK-912 and RX821002 at doses of 12.5 to 25 nmol/kg s.c. are equally effective to antagonise the alpha-2A-adrenoceptor mediated sedation but that their ability to antagonise the alpha-2C-adrenoceptor-mediated hypothermia was different. Therefore, a dose 15 nmol/kg s.c of the both drugs were selected to study the role of alpha2C-adrenoceptor in animal models reflecting stress propagation-induced behavioural changes.

EXPERIMENT 1

Spontaneous motor activity of a single mouse was measured in a polypropylene animal cage (38×22×15 cm) with a transparent polypropylene lid by Photobeam Activity System (PAS, CageRack, San Diego Instruments, San Diego, USA). Temperature was measured by an electronic thermometer with a rectal probe (Ellab A-S, CTD-M, Digital thermometer, Roedovre, Denmark). The animals were injected with various doses of either RX821002 or MK-912 20 min before injection of dexmedetomidine. Spontaneous motor activity was measured 20 min after dexmedetomidine injection and body temperature was measured 30 min after dexmedetomidine injection. The results are presented in FIG. 1, which shows the antagonism of dexmedetomidine-induced sedation (upper graph) and hypothermia (lower graph) by previous administration of RX821002, the alpha-2-adrenoceptor antagonist not selective to the alpha-2C-adrenoceptor, (open bars) or MK-912, the alpha-2-adrenoceptor antagonist selective to the alpha-2C-adrenoceptor (hatched bars).

The following four experiments were carried out in order to verify the role of the alpha-2C-adrenoceptor on the propagation of stress in animals.

EXPERIMENT 2

Drug action on the propagation of a state of behavioural despair in mice

Excessive or prolonged exposure of a test animal to a stressful stimulus has been observed to propagate a state of behavioural despair. For example, a rat or mouse put into a water-filled vessel without any way to escape has an initial intense search for an escape but then the animal gives up (behavioural despair) and starts a moveless float. Among the agents which in subacute treatment conventionally reverse the stress-induced behavioural despair are antidepressive agents (7). Among the agents which conventionally inhibit propagation of stress-induced behavioural despair are anxiolytic agents, such as diazepam (an agonist of GABA-chloride channel-benzodiazepine receptor complex) and dexmedetomidine.

When studying different strains of mice, we found that an NMRI mouse strain tolerates stress and propagation of behavioural despair quite well while a Balb/c mouse strain is very sensitive, as described in literature (8), to stress and propagation of behavioural despair (see Table 1 below). In the NMRI mice it was seen how amount of stress (i.e., duration of forced swim) 24 h before test swim affects propagation of behavioural despair state, reflected in active swimming time. However, the Balb/c strain started to float almost immediately even without any pre-test forced swim period (Table 1).

The test was carried out as follows: Male NMRI or Balb/c mice (Bomholtgard, Denmark) were pre-stressed with different pre-test swim periods 24 h before the test swim. The mice were both drug and experimental naive. Pre-test forced swim periods were of duration of 0, 1, 2.5, 5 or 10 min. The pre-test and test swims were performed in a 1 l vessel (10 cm diameter, 18.5 cm height). The depth of the water was 8 cm, preventing the mice to reach the bottom. The duration of the test swim was 5 min, during which the forced swimming time was measured by a timer clock. After the swim periods, the mice were dried by a paper towel and were kept under a heating lamp for about 15 min. The results are shown in Table 1.

TABLE 1

Difference in NMRI and Bald/c mouse strains in propagation of behavioural despair

| | Active swimming time (±SEM; seconds) after pre-test forced swim periods | | | | |
|---|---|---|---|---|---|
| Strain | 0 min | 1 min | 2.5 min | 5 min | 10 min |
| NMRI | 72 ± 13 | 49 ± 11 | 52 ± 21 | 16 ± 7.2 | 2.0 ± 0.88 |
| Balb/c | 1.3 ± 0.9 | 0.3 ± 0.3 | 0 | 0 | 0 |

When NMRI mice were administered (15 min before pre-test forced swim) with diazepam they tolerated better stress-induced propagation of behavioural despair when measuring their active swim time 24 h later. Dexmedetomidine did not, however, influence propagation of behavioural despair (Table 2). When Balb/c mice (without pre-test forced swim period) were administered (15 min before test swim) with dexmedetomidine or diazepam, they tolerated better stress-induced propagation of behavioural despair (Table 2). These results indicate that these two mouse strains can be used to test different types of medical agents for their stress-induced anxiolytic properties, so that NMRI mice tolerate stress well but the Balb/c mice are very sensitive to stress. Further to these two strains, we found that the stress-sensitivity of the C57BL/6J mouse strain (see below) was in between the NMRI and Balb/c mouse strains.

The tests were performed as described above. Male NMRI mice (B&K, Sweden) were pre-stressed with different pre-test swim periods 24 h before the test swim. Pre-test swim periods were of duration of 0, 2.5 or 5 min. Because pre-test swim could not induce any further behavioural despair in the Balb/c (Bomholtgard, Denmark) strain, these mice were tested without pre-test swim. In experiments with the NMRI mice, drugs were administered s.c. 15 min before the time of the pre-test forced swim. In experiments with the Bald/c mice, drugs were administered s.c. 15 min before the time of the active test swim. The results are shown in Table 2.

TABLE 2

Protective effect of dexmedetomidine (DMD) or diazepam on behavioural despair in NMRI and Bald/c mice

| | Active swimming time (±SEM; seconds) after pre-test forced swim periods | | |
|---|---|---|---|
| Strain | 0 min | 2.5 min | 5 min |
| NMRI | | | |
| Control | 44 ± 7.9 | 2.2 ± 2.0 | 1.2 ± 1.1 |
| DMD 2.5 μg/kg | 36 ± 8.3 | 7.9 ± 3.9 | 6.8 ± 5.1 |
| DMD 5 μg/kg | 29 ± 5.6 | 1.7 ± 1.8 | 9.4 ± 5.1 |
| DMD 10 μg/kg | 36 ± 6.7 | 8.1 ± 3.4 | 3.5 ± 1.7 |
| Diazepam 2 mg/kg | 42 ± 9.5 | 19 ± 9.8 | 15 ± 7.3 |
| Balb/c | | | |
| Control | 0.43 ± 0.23 | | |
| DMD 2.5 μg/kg | 0.36 ± 0.30 | | |
| DMD 5 μg/kg | 1.7 ± 0.72 | | |
| DMD 10 μg/kg | 4.9 ± 2.3 | | |
| Diazepam 1 mg/kg | 6.7 ± 2.4 | | |

The action of the alpha-2C-adrenoceptor antagonist MK-912, in comparison to the non-selective alpha-2-adrenoceptor antagonist RX821002, was studied using the C57BL/6J mouse strain, at a dose (15 nmol/kg s.c.), the dose which differentiates between the alpha-2A and alpha-2C-adrenoceptor-mediated pharmacological responses in vivo (see above). Surprisingly we found that the selective alpha-2C-adrenoceptor antagonist but not the non-selective alpha-2-adrenoceptor antagonist prevented propagation of stress-induced behavioural despair (results shown in FIG. 2) in a manner similar to that seen with dexmedetomidine and diazepam (Table 2).

Figure 2:
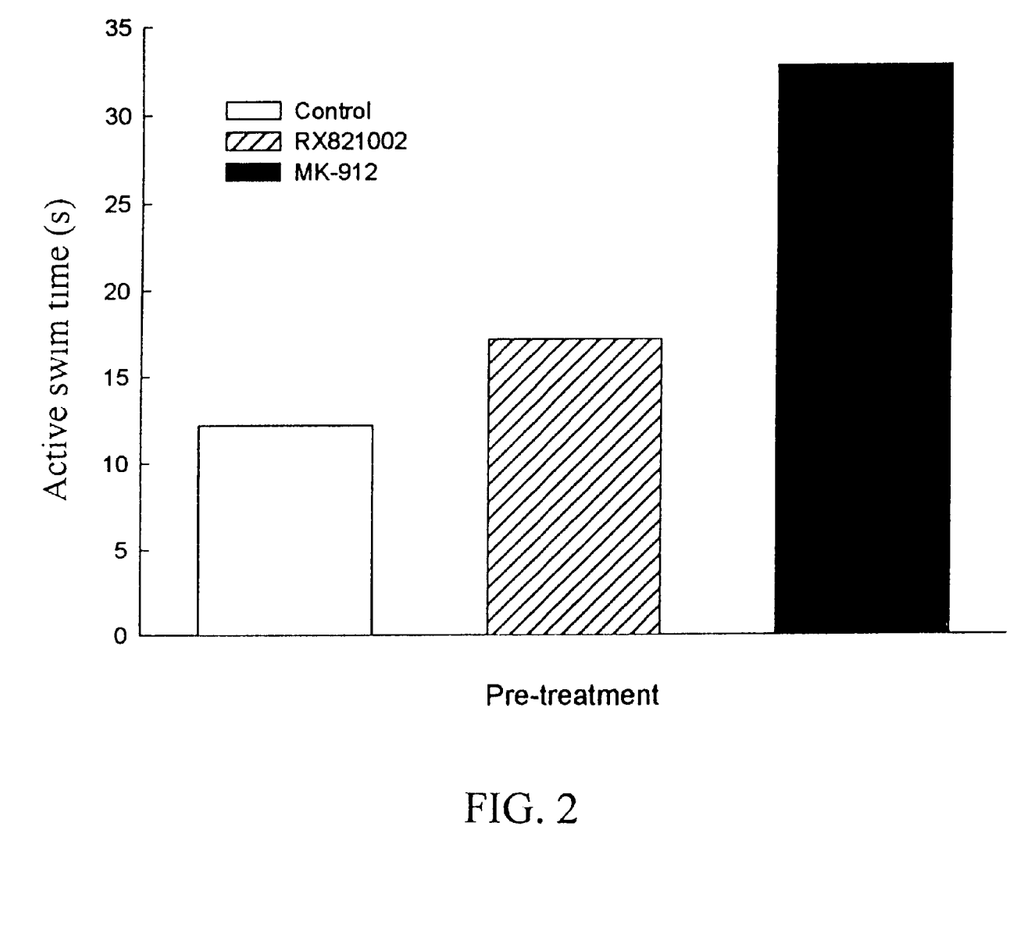
FIG. 2 shows the action of pre-treatment with MK-912, (filled bar), or RX821002 (hatched bar), compared to the control, on forced swim stress-induced behavioural despair in mice.

FIG. 2 shows the action of pre-treatment with the alpha-2C-adrenoceptor antagonist MK-912, 15 nmol/kg (filled bar) or the alpha-2-adrenoceptor antagonist RX821002 not selective to the alpha-2C-adrenoceptor, 15 nmol/kg s.c. (hatched bar) on forced swim stress-induced behavioural despair in mice. C57BL/6J mice were pre-treated either with MK-912 or RX821002 and active swim time was monitored as previously described.

EXPERIMENT 3

Drug action on anxiety in rats

Another conventional test to measure drug action on anxiety is an elevated plus-maze test. In this test, a rat is put in the middle of the plus-maze with two open arms and two closed (with side walls) arms. Rats, typically to rodents, try to avoid exploration of the open arms and prefer the closed arms. Anxiolytic agents, such as diazepam and medetomidine (another alpha-2-adrenoceptor agonist), increase exploratory behaviour and time spent in the open arm area (Table 3), in accordance to what has been described in the literature on these classes of therapeutic agents (9). Typical alpha-2-adrenoceptor antagonists, such as yohimbine and atipamezole, did not increase the exploratory behaviour of rats in the elevated plus-maze test (Table 3).

The test was performed as follows: The plus-maze was made of wood and consisted of two open arms (45×10 cm), two enclosed arms (45×10×40 cm) with an open roof and a central square (10×10 cm). The maze is elevated 55 cm above the floor. Both open arms were divided into three sectors of equal size. On the day of experiment, the rats were brought in their home cage to the experiment room and were allowed to adapt to their surroundings for at least one hour. The experiment room was normally illuminated and kept quiet. Eight rats (16 in the control group) were assigned to each dose of drugs which were administered s.c. (or their control solution, Intralipid for diazepam and distilled water for others). The sequence of different doses was randomised by a Latin Square technique, the experimenter being kept blinded for the doses used. After the injection the rat was put back to its home cage, but after 20 min the rat was placed on the central square of the plus-maze so that the rat was facing the enclosed arm. The rat behaviour was observed for 10 min and the number of sectors crossed on open arms and the cumulative time spent on the open arms were recorded. The results are shown in Table 3. Data are means ±SEM.

TABLE 3

Action of diazepam, medetomidine, yohimbine and atipamezole in the elevated plus-maze test in rats

| Treatment | Open-arms' lines crossed | Time spent in open arms(s) |
|---|---|---|
| Control | 0.30 ± 0.30 | 5.1 ± 1.7 |
| Diazepam 1 mg/kg | 7.9 ± 1.5 | 70 ± 15 |
| Medetomidine 3 μg/kg | 3.4 ± 1.9 | 34 ± 10 |
| Medetomidine 10 μg/kg | 4.1 ± 2.4 | 46 ± 16 |
| Yohimbine 0.1 mg/kg | 0.30 ± 0.30 | 17 ± 7.6 |
| Yohimbine 0.3 mg/kg | 0.80 ± 0.50 | 13 ± 6.2 |
| Yohimbine 1 mg/kg | 0.50 ± 0.50 | 10 ± 50 |
| Yohimbine 3 mg/kg | 0.30 ± 0.30 | 2.4 ± 1.6 |
| Atipamezole 0.03 | 0.90 ± 0.50 | 11 ± 5.4 |

TABLE 3-continued

Action of diazepam, medetomidine, yohimbine and atipamezole in the elevated plus-maze test in rats

| Treatment | Open-arms' lines crossed | Time spent in open arms(s) |
|---|---|---|
| mg/kg | | |
| Atipamezole 0.1 mg/kg | 0.50 ± 0.50 | 7.6 ± 6.2 |
| Atipamezole 0.3 mg/kg | 0.50 ± 0.50 | 1.9 ± 1.9 |

Using the alpha-2C-adrenoceptor selective dose of MK-912, this drug had response similar to that of other anxiolytic agents. On the other hand, similar to the other typical non-selective alpha-2-adrenoceptor antagonists, RX821002 (15 nmol/kg s.c.) did not provide any anxiolytic response, by affecting neither exploratory behaviour nor time spent on open arms in elevated plus maze (FIGS. 3A and 3B).

Figure 3A:
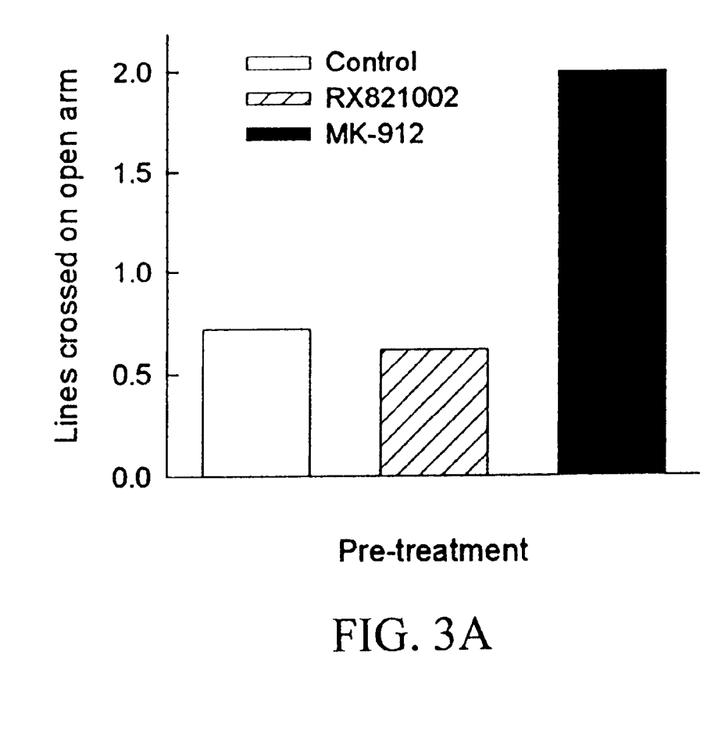
FIG. 3A and 3B show the action of pre-treatment with MK-912 (filled bar) or RX821002 (hatched bar), compared to the control, on exploratory behaviour in rats in an elevated plus-maze test.
Figure 3B:
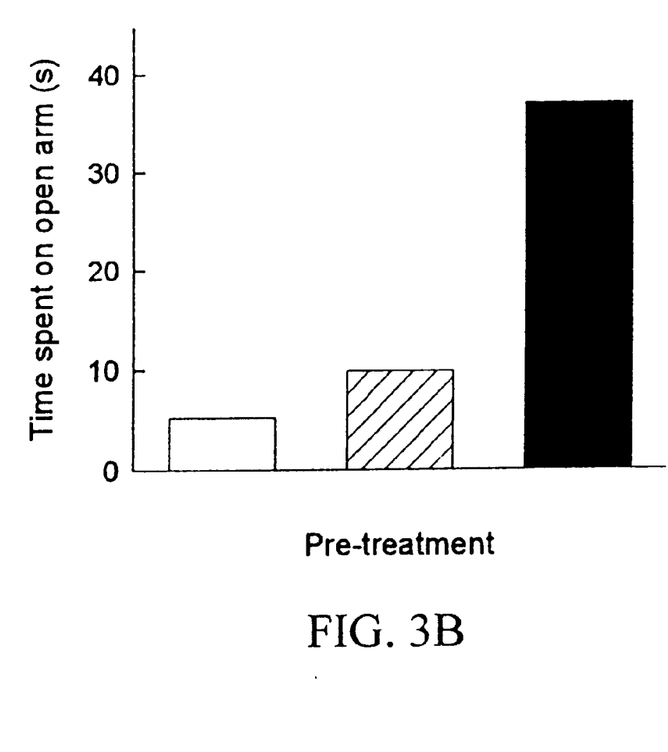

FIGS. 3A and 3B show the action of pre-treatment with 15 nmol/kg s.c. of MK-912 (filled bar) or 15 nmol/kg s.c. of RX821002 (hatched bar) on exploratory behaviour in rats in an elevated plus-maze test carried out as described above. Arithmetic mean values are given. FIG. 3A shows the number of lines crossed on open arm and FIG. 3B shows the time spent on open arm.

EXPERIMENT 4
Drug action on neophobic stress-induced exploratory behaviour in rats A staircase test is also used to study neophobic stress-induced exploratory behaviour in rodents (10). Rats, as described above, are neophobic and cautiously approach an unknown territory. In a staircase test, a rat is put into a box containing stairs. In this test, anxiolytic agents (such as diazepam and medetomidine) decrease neophobic stress and rats access more steps in the stairs (Table 4), indicating increased exploratory behaviour. Therapeutic dose ranges of diazepam and medetomidine are typically quite narrow because they avidly impair motor functions and vigilance, which is also clinically obvious. In this test, non-subtype selective alpha-2-adrenoceptor antagonists like yohimbine and atipamezole potentiate neophobic stress in the animals and less steps are accessed. In contrast to these non-subtype selective alpha-2-adrenoceptor antagonists and to that of RX821002, the alpha-2C-adrenoceptor antagonist MK-912 (at the subtype selective dose 15 nmol/kg s.c.) does not potentiate neophobic stress but augments exploratory behaviour as anxiolytics do (Table 4).

The experiment was performed as follows: The apparatus consisted of an enclosed wooden staircase as described (10). It was composed of five identical steps 5 cm high, 20 cm wide and 15 cm deep. The internal height of walls (25 cm) was constant along the whole length of the staircase. On the day of experiment, the rats were brought inside their home cage to the experiment room and were allowed to adapt to its surroundings for one hour. The experiment room was normally illuminated and kept quiet. Drugs and control solutions were injected 20 min before testing. After the injection the rats were put back to their home cages. Eight rats were assigned to each dose. The drugs were tested at different days and every time had a new (own) control group. The test solutions were kept in coded bottles, so the investigator was blinded to the doses. The sequence of different doses was randomised by Latin Square. At the beginning of the test the rat was placed on the ground floor of the apparatus with its back to the stairs and the number of steps climbed was scored (downward steps were not counted) for 3 min. A step was counted when the rat completely ascended the step, placing all four paws onto the step. The results are given in Table 4.

TABLE 4

Action of diazepam, medetomidine, yohimbine, atipamezole, RX821002 and MK-912 in the staircase test in rats.

| Treatment | Steps climbed (% of control) |
|---|---|
| Control | (100) |
| Diazepam 0.3 mg/kg | 111 |
| Diazepam 1 mg/kg | 143 |
| Diazepam 3 mg/kg | 71 |
| Medetomidine 3 µg/kg | 131 |
| Medetomidine 10 µg/kg | 160 |
| Medetomidine 30 µg/kg | 55 |
| Yohimbine 0.3 mg/kg | 79 |
| Yohimbine 1 mg/kg | 83 |
| Yohimbine 3 mg/kg | 33 |
| Atipamezole 0.03 mg/kg | 54 |
| Atipamezole 0.1 mg/kg | 42 |
| Atipamezole 0.3 mg/kg | 25 |
| RX821002 15 nmol/kg | 49 |
| MK-912 15 nmol/kg | 112 |

EXPERIMENT 5
Propagation of a state of behavioural despair in transgenic mice A fourth piece of evidence supporting the notion of blockade of alpha-2C-adrenoceptor in providing protection against stress-induced anxiety and mental despair comes from experiments with transgenic mice with genetic manipulations in expression of the alpha-2C-adrenoceptor (11). Using targeted disruption a mutation of the gene encoding the alpha-2C-adrenoceptor was made, generating an alpha-2C-adrenoceptor knock-out mouse strain (alpha-2C-KO mice). Using a pronuclear injection technique overexpression of the gene encoding the alpha-2C-adrenoceptor was made, generating an alpha-2C-adrenoceptor overexpression mouse strain (alpha-2C-OE mice). The alpha-2C-KO and alpha-2C-OE mice were tested for their characteristics in stress-induced behavioural despair in the swim test described in Experiment 2. In accordance with the drug-derived experiments described above, genetic alterations in the expression of the alpha-2C-adrenoceptor were respectively reflected in propagation of stress-induced behavioural despair (FIGS. 4A and 4B).

Figure 4A:
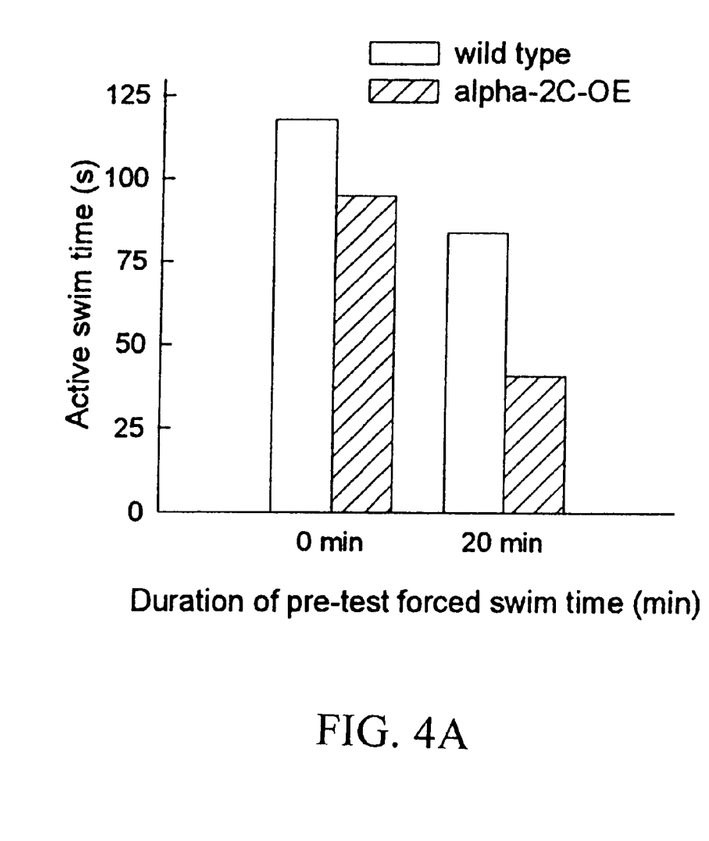
FIG. 4A shows the predisposition to stress-induced propagation of behavioural despair in transgenic mice over-expressing the alpha-2C-adrenoceptor (hatched bar) compared to their wild type genetic controls (open bar).
Figure 4B:
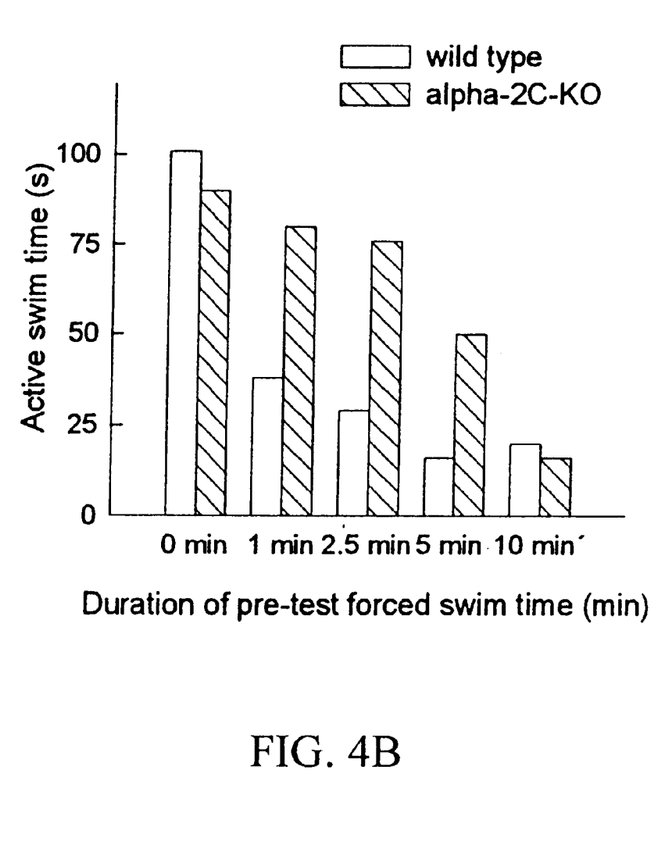
FIG. 4B shows the predisposition to stress-induced propagation of behavioural despair in transgenic mice without alpha-2C-adrenoceptor expression (hatched bar) compared to their wild type genetic controls (open bar).

FIGS. 4A and 4B show the effect of alteration of the alpha-2C-adrenoceptor function at the gene expression level. Transgenic mice overexpressing the alpha-2C-adrenoceptor (FIG. 4A, hatched bar) were predisposed to stress-induced propagation of behavioural despair compared to their wild type genetic controls (FIG. 4A, open bar). On the other hand, transgenic mice without alpha-2C-adrenoceptor expression (FIG. 4B, hatched bar) were protected against stress-induced behavioural despair, as compared to their control group (FIG. 4B, open bar).

It will be appreciated that the methods of the present invention can be incorporated in the form of a variety of embodiments, only a few of which are disclosed herein. It will be apparent for the specialist in the field that other embodiments exist and do not depart from the spirit of the invention. Thus, the described embodiments are illustrative and should not be construed as restrictive.

REFERENCES

1. Charney, D. S., G. R. Heninger, and A. Breier, Noradrenergic function in panic anxiety. Effects of yohimbine in healthy subjects and patients with agoraphobia and panic disorder (1984) Arch Gen Psych, 41, 751–763; Charney, D. S., A. Breier, P. I. Jatlow, and G. R. Heninger, Behavioral, biochemical, and blood pressure responses to alprazolam in healthy subjects: interactions with yohimbine (1986) Psychopharmacology, 88, 133–140.
2. Scheinin, M., Lomasney, J. W., Hayden-Hixson, D. M., Schambra, U. B., Caron, M. G., Lefkowitz, R. J., & Fremeau, R. T., Jr. (1994). Distribution of $\alpha_2$-adrenergic receptor subtype gene expression in rat brain. Mol Brain Res, 21, 133–149; Wamsley, J. K., Alburges, M. E., Hunt, M. A. E., & Bylund, D. B. (1992). Differential localization of $\alpha_2$-adrenergic receptor subtypes in brain. Pharmacol Biochem Behav, 41, 267–273; de Vos, H., Vauquelin, G., De Keyser, J., de Backer, J.-P., & Van Liefde, I. (1992). Regional distribution of $\alpha_{2A}$- and $\alpha_{2B}$- adrenoceptor subtypes in postmortem human brain. J Neurochem, 58, 1555–1560; Nicholas, A. P., Pieribone, V., & Hökfelt, T. (1993). Distributions of mRNAs for alpha-2 adrenergic receptor subtypes in rat brain: An in situ hybridization study. J Comp Neurol, 328, 575–594.
3. Guo, T. Z., Jiang, J. Y., Buttermann, A. E., & Maze, M. (1996). Dexmedetomidine injection into the locus ceruleus produces antinociception. Anesthesiology, 84, 873–881; Scheinin, M., & Schwinn, D. A. (1992). The locus coeruleus. Site for hypnotic actions of $\alpha_2$-adrenoceptor agonists? Anesthesiology, 76, 873–875; Scheinin, M., Lomasney, J. W., Hayden-Hixson, D. M., Schambra, U. B., Caron, M. G., Lefkowitz, R. J., & Fremeau, R. T., Jr. (1994). Distribution of $\alpha_2$-adrenergic receptor subtype gene expression in rat brain. Mol Brain Res, 21, 133–149.
4. Sallinen, J., Link, R. E., Haapalinna, A., Viitamaa, T., Kulatunga, M., Sjöholm, B., MacDonald, E., Leino, T., Barsh, G. S., Kobilka, B. K., & Scheinin, M. (1997). Genetic alteration of alpha-2C-adrenoceptor expression in mice: influence on locomotor, hypothermic, and neurochemical effects of dexmedetomidine, a subtype-nonselective alpha-2-adrenoceptor agonist. Mol Pharmacol, 51, 36–46.
5. Uhlen, S., Muceniece, R., Rangel, N., Tiger, G., Wikberg, J. E. S. (1995) Comparison of the binding activities of some drugs on alpha2A, alpha2B and alpha2C-adrenoceptors and non-adrenergic imidazoline sites in the guinea pig. Pharmacol Toxicol, 76, 353–364; Uhlen, S., Porter, A. C., Neubig, R. R. (1994) The novel alpha-2 adrenergic radioligand [$^3$H]-MK912 is alpha-2C selective among human alpha-2A, alpha-2B and alpha-2C adrenoceptors. J Pharmacol Exp Ther, 271, 1558–1565.
6. Marjamäki, A., Luomala, K., Ala-Uotila, S., & Scheinin, M. (1993). Use of recombinant human $\alpha_2$-adrenoceptors to characterize subtype selectivity of antagonist binding. Eur J Pharmacol-Molec Pharm, 246, 219–226; Devedjian, J.-C., Esclapez, F., Denis-Pouxviel, C., & Paris, H. (1994). Further characterization of human $\alpha_2$-adrenoceptor subtypes: [$^3$H]RX821002 binding and definition of additional selective drugs. Eur J Pharmacol, 252, 43–49; O'Rourke, M. F., Blaxall, H. S., Iversen, L. J., & Bylund, D. B. (1994). Characterization of [$^3$H] RX821002 binding to alpha-2 adrenergic receptor subtypes J Pharmacol Exp Ther, 268, 1362–1367; Halme, M., Sjöholm, B., Savola, J.-M., & Scheinin, M. (1995). Recombinant human $\alpha_2$-adrenoceptor subtypes: comparison of [$^3$H]rauwolscine, [$^3$H]atipamezole and [$^3$H] RX821002 as radioligands. Biochim Biophys Acta, 1266, 207–214.
7. Porsolt, R. D., A. Bertin, and M. Jalfre (1977) Behavioural despair in mice: a primary screening test for antidepressants. Arch. int. Pharmacodyn., 229, 327–335; Porsolt, R. D., G. Anton, N. Blavet, and M. Jalfre (1978) Behavioural despair in rats: a new model sensitive to antidepressant treatments. Eur J Pharmacol, 47, 379–391.
8. Crawley, J. N. & Davis, L. G. (1982) Baseline exploratory activity predicts anxiolytic responsiveness to diazepam in five mouse strains. Brain Res Bulletin, 8, 609–612.
9. Salonen, M., Reid, K., & Maze, M. (1992). Synergistic interaction between $\alpha_2$-adrenergic agonists and benzodiazepines in rats. Anesthesiology, 76, 1004–1011; Salonen, M., Onaivi, E. S., & Maze, M. (1992). Dexmedetomidine synergism with midazolam in the elevated plus-maze test in rats. Psychopharmacology (Berl), 108, 229–234.
10. Stéru, L., B. Thierry, R. Chermat, B. Millet, P. Simon, and R. D. Porsolt (1987) Comparing benzodiazepines using the staircase test in mice. Psychopharmacology, 92, 106–109.
11. Link, R. E., Stevens, M. S., Kulatunga, M., Scheinin, M., Barsh, G. S., & Kobilka, B. K. (1995). Targeted inactivation of the gene encoding the mouse $\alpha_{2C}$-adrenoceptor homolog. Mol Pharmacol, 48, 48–55; Sallinen, J., Link, R. E., Haapalinna, A., Viitamaa, T., Kulatunga, M., Sjöholm, B., MacDonald, E., Leino, T., Barsh, G. S., Kobilka, B. K., & Scheinin, M. (1997). Genetic alteration of alpha-2C-adrenoceptor expression in mice: influence on locomotor, hypothermic, and neurochemical effects of dexmedetomidine, a subtype-nonselective alpha-2-adrenoceptor agonist. Mol Pharmacol, 51, 36–46.
12. Blaxall, H. S., Murphy, T. J., Baker, J. C., Ray, C. & Bylund, D. B. (1991). Characterization of the alpha-2C adrenergic receptor subtype in the opossum kidney and in the OK cell line. J Pharmacol Exp Ther, 259, 323–329.

We claim:

1. A method for treating mental illness induced by stress in a mammal in need thereof, wherein said method comprises administering a therapeutically effective amount of an alpha-2-adrenoceptor antagonist or a derivative thereof, wherein said alpha-2-adrenoceptor antagonist is selective for the alpha-2C-adrenoceptor subtype.

2. The method according to claim 1 wherein said mental illness is clinically expressed as a disorder selected from the group consisting of anxiety, stress, post-traumatic stress disorder, depression, affective flattening, anhedonia, alogia, avolition, aggressivity, and impairment of cognitive function initiated by stress-induced neuronal degeneration.

3. The method according to claim 1, wherein the administering of said alpha-2-adrenoceptor antagonist selective for the alpha-2C-adrenoceptor subtype is combined with the administering of a different therapeutically active compound or a derivative thereof, wherein said different therapeutically active compound is an anxiolytic, an antidepressive or an antipsychotic compound.

4. The method according to claim 3, wherein said alpha-2-adrenoceptor antagonist selective for the alpha-2C-adrenoceptor subtype and said different therapeutically active compound are administered during the same period of treatment.

5. The method according to claim 4, wherein said alpha-2-adrenoceptor antagonist selective for the alpha-2C-adrenoceptor subtype and said different therapeutically active compound are administered simultaneously.

6. The method according to claim 5, wherein said alpha-2-adrenoceptor antagonist selective for the alpha-2C-adrenoceptor subtype and said different therapeutically active compound are administered from a common dosage form.

7. The method according to any one of claims 1, 2, or 3–5, wherein said alpha-2-adrenoceptor antagonist is at least ten-fold more selective for the alpha-2C-adrenoceptor subtype than for other alpha-2-subtypes.

8. A pharmaceutical composition useful for the treatment of a mental illness induced by stress in a mammal, wherein said composition comprises a therapeutically effective amount of an alpha-2-adrenoceptor antagonist or a derivative thereof, said antagonist being selective for the alpha-2C-adrenoceptor subtype, in combination with a pharmaceutically acceptable excipient, wherein said composition further comprises a therapeutically effective amount of a different compound or a derivative thereof, wherein said different compound, which does not need to be antagonist selective for the alpha-2C-adrenoceptor subtype, is an anxiolytic, an antidepressive or an antipsychotic compound.

9. The composition according to claim 8, wherein said alpha-2-adrenoceptor antagonist is at least ten-fold more selective for the alpha-2C-adrenoceptor subtype than for other alpha-2-subtypes.

10. A method of preventing a mental illness induced by stress in a mammal in need thereof, wherein said method comprises administering a therapeutically effective amount of an alpha-2-adrenoceptor antagonist selective for the alpha-2C-adrenoceptor subtype to the mammal.

11. The method according to claim 10, wherein said mental illness is clinically expressed as a disorder selected from the group consisting of anxiety, stress, post-traumatic stress disorder, depression, affective flattening, anhedonia, alogia, avolition, aggressivity, and impairment of cognitive function initiated by stress-induced neuronal degeneration.

12. The method according to claim 10 or 11, wherein said alpha-2-adrenoceptor antagonist is at least ten-fold more selective for the alpha-2C-adrenoceptor subtype than for other alpha-2-subtypes.

* * * * *